United States Patent [19]

Komiyama et al.

[11] 4,066,402
[45] Jan. 3, 1978

[54] ANALYTICAL METHOD AND APPARATUS FOR DETERMINATION OF TOTAL NITROGEN AND/OR CARBON CONTENTS IN AQUEOUS SYSTEMS

[75] Inventors: Yoshiki Komiyama, Takatsuki; Seiya Yamamoto, Ashiya; Yoshiaki Yasumasa, Toyonaka, all of Japan

[73] Assignee: Sumitomo Chemical Company, Limited, Osaka, Japan

[21] Appl. No.: 686,635

[22] Filed: May 14, 1976

[30] Foreign Application Priority Data

May 15, 1975 Japan .................... 50-58339

[51] Int. Cl.² ................ G01N 33/18; G01N 1/10; G01N 27/18
[52] U.S. Cl. ............... 23/230 PC; 23/253 PC; 23/232 E; 23/254 E
[58] Field of Search ........ 23/232 C, 230 PC, 253 PC, 23/254 E, 232 E, 230 R, 232 R, 254 R; 73/23.1, 26

[56] References Cited

U.S. PATENT DOCUMENTS

| | | |
|---|---|---|
| 3,096,157 | 7/1963 | Brown et al. .................. 23/232 C |
| 3,097,518 | 7/1963 | Taylor et al. .................. 23/232 C |
| 3,296,435 | 1/1967 | Teal et al. ..................... 23/230 PC |
| 3,304,159 | 2/1967 | Hinsuark ....................... 23/232 C |
| 3,567,386 | 3/1971 | Stenger ......................... 23/230 PC |
| 3,607,071 | 9/1971 | Staffin .......................... 23/230 PC |
| 3,958,937 | 5/1976 | Shibata et al. ................ 23/253 PC |

Primary Examiner—R.E. Serwin
Attorney, Agent, or Firm—Birch, Stewart, Kolasch and Birch

[57] ABSTRACT

An analytical method for determining rapidly and accurately the total nitrogen and/or carbon contents in aqueous systems containing nitrogenous and/or carbonaceous materials, which comprises introducing an aqueous solution containing nitrogenous and/or carbonaceous materials as a specimen to be analyzed together with a carrier gas into a reactor tube packed with a destructive oxidation catalyst and/or a reducing agent and/or an oxidizing agent and maintaining said solution at certain elevated temperatures so as to decompose the nitrogenous and/or carbonaceous materials to nitrogen and/or carbon dioxide and measuring the amounts of nitrogen and/or carbon dioxide in the resulting gaseous mixture by the use of a thermal conductivity gas chromatograph, and an apparatus to be used for carrying out such method.

25 Claims, 2 Drawing Figures

ANALYTICAL METHOD AND APPARATUS FOR DETERMINATION OF TOTAL NITROGEN AND/OR CARBON CONTENTS IN AQUEOUS SYSTEMS

BACKGROUND AND SUMMARY OF THE INVENTION

The present invention relates to an analytical method and apparatus for determining the total nitrogen and/or carbon contents in aqueous systems such as waste water.

With respect to environmental pollution problems, there has been highly sought the appearance of an analytical method and apparatus for determining rapidly and accurately the total contents of nitrogen, carbon, phosphorus, sulfur, etc. in "aqueous" systems by element, which may constitute the source of nutritional enrichment or red water in waters.

For analyzing the total nitrogen content in aqueous systems, there are known the so-called wet chemical methods, which however require an extremely long time for measurement. Further, in order to obtain accurate analytical values, sufficient knowledges on the reactions applied to the analysis and the influences to be caused by co-existing components are necessary. Furthermore, the persons who carry out the analytical methods are required to have highly technical skill. There are also proposed some analytical methods using instruments such as a method for detection of ammonia produced from hydrogenative decomposition of nitrogenous materials by coulometry, a method for the detection of chemical fluorescence on the formation of nitrogen dioxide by the reaction of nitrogen monoxide derived from nitrogenous materials with ozone and a method for detection of nitrogen monoxide produced from nitrogenous materials by the use of an infrared analyzer.

On the other hand, as to the analysis of the total carbon content in aqueous systems, there are known a method wherein carbonaceous materials are decomposed in a carrier gas containing oxygen at high temperatures and the resulting carbon dioxide is quantitatively determined (U.S. Pat. No. 3,296,435), a method wherein carbonaceous materials are decomposed in a carrier gas containing no oxygen in the presence of a catalyst such as palladium at elevated temperatures and the resulting carbon dioxide is determined quantitatively by means of an infrared analyzer (U.S. Pat. No. 3,530,292), etc. These methods are, however, disadvantageous in using an infrared analyzer, which is still expensive. Analytical methods using a gas chromatograph instead of the use of an infrared analyzer are proposed, but they are defective on the operation or the safety, because the gas produced by decomposition is stored once in a holder to make uniform and then subjected to analysis, or measurement is made by the use of a hydrogen flame ionization detector utilizing dangerous hydrogen gas.

For the simultaneous determination of the total nitrogen and carbon contents, there are proposed only few methods, of which a typical one is based on the principle of an elemental analyzer for carbon, hydrogen and nitrogen and comprises subjecting carbonaceous materials to combustion in the presence of oxygen and subjecting nitrogenous materials to reduction, followed by determination of the amounts of the resultant carbon dioxide and nitrogen using a gas chromatograph. However, this method requires a special and complicated device for the supply of oxygen gas.

A basic object of the present invention is to provide an analytical method for the determination of the total nitrogen and/or carbon contents in aqueous systems containing nitrogenous and/or carbonaceous materials. Another object of the present invention is to provide an analytical method for determining rapidly and accurately the total nitrogen and carbon contents in aqueous systems containing nitrogenous and carbonaceous materials by a simple operation. A further object of the present invention is to provide an analytical apparatus for determination of the total nitrogen and/or carbon contents in aqueous systems containing nitrogenous and/or carbonaceous materials. A still further object of the present invention is to provide an analytical apparatus for determining rapidly and accurately the total nitrogen and carbon contents in aqueous systems containing nitrogenous and carbonaceous materials which comprises readily available and less expensive instruments. These and other objects of the present invention will be apparent to those skilled in the art from the foregoing and subsequent descriptions.

The analytical method of the present invention comprises introducing an aqueous solution containing nitrogenous and/or carbonaceous materials as a specimen to be analyzed together with a carrier gas into a reactor tube packed with a destructive oxidation catalyst and/or a reducing agent and/or an oxidizing agent and maintained at certain elevated temperatures so as to decompose the nitrogenous and/or carbonaceous materials to nitrogen and/or carbon dioxide and measuring the amounts of nitrogen and/or carbon dioxide in the resulting gaseous mixture by the use of a thermal conductivity gas chromatograph.

The said analytical method may be carried out by the use of an apparatus which comprises a reactor tube provided with an inlet and an outlet through which a carrier gas is passed and packed with a destructive oxidation catalyst and/or a reducing agent and/or an oxidizing agent, a means for injecting a specimen to be analyzed into the reactor tube, a means for supplying an inert gas as the carrier gas into the reactor tube, a means for removal of moisture from the gaseous mixture produced in the reactor tube and a gas chromatograph provided with a thermal conductivity detector.

A specimen to be analyzed, which is an aqueous solution containing nitrogenous and/or carbonaceous materials, is introduced from the injector means into the reactor tube, usually through the inlet for the carrier gas.

Examples of the inert gas as the carrier gas are helium, argon, etc. Preferred is helium, because it has a larger difference from nitrogen and carbon dioxide in thermal conductivity. When the determination of the total carbon content is intended, nitrogen may be also used as the carrier gas. In case of the determination of the total nitrogen content with or without the total carbon content, however, nitrogen can not be used as the carrier gas. The inert gas from the supply means is introduced into the reactor tube, usually at a flow rate of about 20 to 200 ml/min.

The reactor tube may be made of a heat and corrosion resistant material such as quartz or ceramics (e.g. mullite). While no particular limitation exists on the size of the reactor tube, a typical example of practically utilizable reactor tubes is the one having an inner diameter of about 7 to 13 mm and an inner volume of about 20 to 50 ml.

The reactor tube is packed with a destructive oxidation catalyst and/or a reducing agent and/or an oxidizing agent. When only the determination of the total nitrogen content is intended, the reactor tube may be packed with a destructive oxidation catalyst and a reducing agent. In this case, the destructive oxidation catalyst is to be positioned on the side of the inlet and the reducing agent on the side of the outlet. When only the determination of the total carbon content is intended, the oxidizing agent alone or together with the destructive oxidation catalyst may be packed into the reactor tube. For accelerating the decomposition of carbonaceous materials and avoiding the pulverization of the oxidizing agent, it is usually preferred to use the oxidizing agent with the destructive oxidation which is positioned on the side of the inlet. In case of the determination of the total contents of nitrogen and carbon being aimed at, the destructive oxidization catalyst, the reducing agent and the oxidizing agent are packed in the reactor tube. Preferably, these materials may be arranged in the said order in the reactor tube from the inlet side to the outlet side.

The reactor tube is heated by a conventional heating means so as to maintain the zone packed with the destructive oxidation catalyst at a temperature of from about 700° to 1200° C (preferably from about 700° to 1000° C) and the zone(s) packed with the reducing agent and/or the oxidizing agent at a temperature of from about 300° to 700° C. When only the oxidizing agent (i.e. without the destructive oxidation catalyst and the reducing agent) is used as the packing material, it may be heated at a temperature of from about 700° to 1200° C.

As the destructive oxidation catalyst, there may be used the one comprising at least one metal belonging to Group IB or VIII in the periodic table. In view of the high stability at elevated temperatures, the use of a platinum group metal such as platinum or palladium is favorable. The destructive oxidation catalyst may be employed in any conventional form which does not prevent the flow of a gaseous material (e.g. pellets, wires, gauzes). When desired, the destructive oxidation catalyst may be the metal deposited on a conventional carrier material (e.g. asbestos, alumina). The destructive oxidation catalyst heated at a temperature from about 700° to 1200° C can decompose nitrogenous and carbonaceous materials in cooperation with the oxidizing action of water at such high temperature to produce lower molecular compounds, of which portions are further converted into nitrogen and carbon dioxide.

As the reducing agent, there may be used the one comprising at least one of copper, nickel, iron, cobalt and zinc. In view of the high reducing power, preferred are reduced copper or reduced nickel. The reducing agent may be employed in any conventional form (e.g. pellets, wires, gauzes). The reducing agent heated at a temperature of from about 300° to 700° C is effective in converting nitrogenous oxides present in the gaseous mixture coming through the preceding zone of the destructive oxidation catalyst into nitrogen and also in eliminating oxygen in the said gaseous mixture.

As the oxidizing agent, there may be used the one comprising at least one of oxides of cobalt, nickel, vanadium, tungsten, silver and manganese. They may be used alone or in combination. A typical example of their mixture is hopcalite, i.e. a mixture of manganese oxide, copper oxide, cobalt oxide and silver oxide. In view of the high oxidizing power at elevated temperatures, the use of oxides of cobalt is preferred. The form of the oxidizing agent may be any conventional one (e.g. pellets, wires, gauzes). The oxidizing agent heated at a temperature of from about 300° to 700° C accomplishes the conversion of the incompletely oxidized carbonaceous compounds present in the gaseous mixture coming through the preceding zone of the destructive oxidation catalyst to the completely oxidized carbonaceous compound, i.e. carbon dioxide.

In the reactor tube, the nitrogenous and/or carbonaceous materials are decomposed to nitrogen and/or carbon dioxide. The gaseous mixture comprising these gaseous materials flows out from the reactor tube through the outlet and is led into the means for removal of moisture. As the means for removal of water, there may be employed any conventional one such as a tube packed with a dehydrating agent (e.g. magnesium perchlorate, phosphorus pentoxide, ion exchange resin) or an electronic cooler.

Then, the gaseous mixture made moisture-free is sent to the thermal conductivity gas chromatograph for detecting nitrogen and carbon dioxide, which may be any conventional one. Both of a single column passage type and a double column passage type are utilizable. In the separation column, any conventional packing material for gas chromatography may be used, and specific examples are silica gel, activated carbon, porous polymer beads, etc.

The analytical method and apparatus of the present invention will be hereinafter illustrated in details with reference to FIG. 1 of the accompanying drawings which is a block diagram showing an embodiment of the invention in case of determining the total nitrogen and carbon contents.

Figure 1:
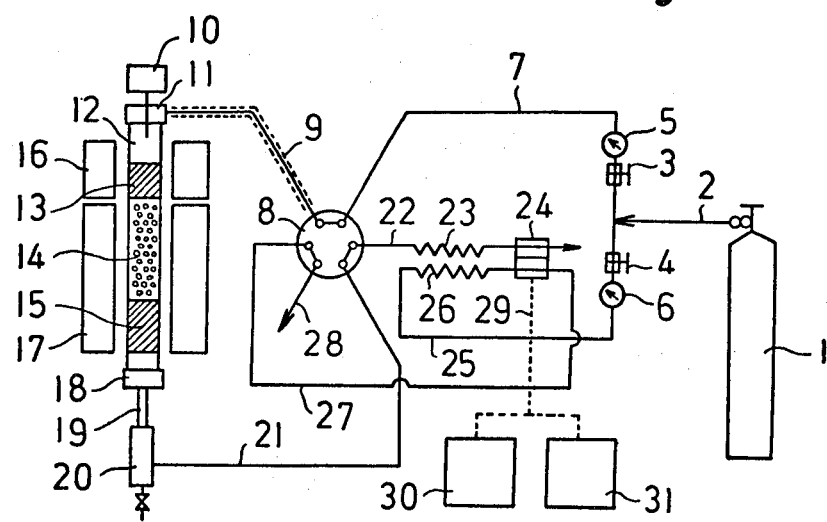
FIG. 1 is a block diagram of the apparatus.

In FIG. 1, an inert gas (e.g. helium) available as the carrier gas from a gas cylinder 1 flows through a conduit 2 and branches into two directions. In one direction, the gas is led at a constant flow rate through a pressure controller 4, a pressure gauge 6 and a conduit 25 into the reference side of a gas chromatograph. In the other direction, the gas runs at a constant flow rate through a pressure controller 3 and a pressure gauge 5 to a conduit 7. Element 8 is a cock which is, in FIG. 1, in the state of measurement. A reactor tube 12 is provided with an inlet 11 and an outlet 18 for the carrier gas. The inlet 11 also serves to introduce a specimen to be analyzed therethrough. In the reactor tube 12, 13 is a destructive oxidation catalyst zone, 14 is a reducing agent zone and 15 is an oxidizing agent zone. Furnaces 16 and 17 are provided for heating the destructive oxidation catalyst zone and the zones of the reducing agent, respectively and of the oxidizing agent to maintain those zones at certain elevated temperatures.

An aqueous solution containing nitrogenous and carbonaceous materials (usually about 10 to 100 μl) as the specimem is introduced into the reactor tube 12 from the inlet 11 by the use of an appropriate supply means 10 such as a microsyringe or an automatic weighing injector. The gaseous mixture formed in the reactor tube 12 is carried on with the carrier gas through the outlet 18 and a conduit 19 to a moisture removal means 20. The gaseous mixture, after removal of the moisture, is sent through a conduit 21, the cock 8 and a conduit 22 into a thermal conductivity gas chromatograph wherein separation columns 23 and 26 are packed with packing materials. The signal obtained from a thermal conductivity detector 24 is recorded on a recorder 30 through a signal line 29.

Analysis may be made on the basis of the peak area or the peak height in the recorded chromatogram. The total nitrogen and carbon contents in the specimen can be directly recorded by a data analysis apparatus 31 such as a digital integrator. The cock 8 is provided for separation of the gas chromatograph on the replacement of the materials packed in the reactor tube 12. When the cock 8 is changed from the state as indicated in FIG. 1, the conduit 7 is connected to the conduit 22 so that the carrier gas flows directly into the gas chromatograph. The conduits 27 and 21 are respectively connected with the conduits 9 and 28, whereby communication to atmosphere is made. The conduit 9 is heated, for instance, at about 120° C for preventing the condensation of water resulting from the partial back current of the gaseous mixture on the injection of the specimen.

Advantageously, the analytical method of the invention can determine the total nitrogen and/or carbon contents in aqueous systems including nitrogenous and/or carbonaceous materials rapidly and accurately by the use of a simple apparatus without any high technical skill or experience as well as any special knowledge. Irrespective of the state of the nitrogenous and/or carbonaceous materials existing in aqueous systems and even in the presence of such high concentrations of salts as in sea water, it is applicable to the determination of the total nitrogen and/or carbon contents. Also, the total organic carbon content can be readily determined by treatment of the specimen with an inorganic acid such as hydrochloric acid for decarboxylation or by using an apparatus for measurement of inorganic carbon in combination.

Since the apparatus of the invention is quite simple, its maintenance can be made easily. Further, it can be made automatic without any difficulty, and the continuous monitoring of the total nitrogen and/or carbon contents in various aqueous systems becomes possible.

Practical and presently preferred embodiments of the present invention are illustratively shown in the following Examples.

EXAMPLE 1

The apparatus as shown in FIG. 1 of the accompanying drawings was used.

In a mullite pipe of 10.5 mm in inner diameter and 30 cm in length as the reactor tube, cylindrical platinum guaze (60 mesh; 5 cm in length) as the destructive oxidation catalyst, reduced copper wire (about 8 ml; 0.6 mm in diameter; 5 mm in length) as the reducing agent and pelletized tricobalt tetroxide (about 6 ml; 10 to 24 mesh) as the oxidizing agent were charged separating each material from others with quartz cotton and also placing quartz cotton at the lowest part. The destructive oxidation catalyst zone was kept at 950° C, and the reducing agent zone and the oxidizing agent zone were maintained at 500° C. In a stainless steel column of 1 m in length as the separation column in the gas chromatograph, silica gel (60 to 80 mesh) was charged, and the temperature of the column was set at 80° C. The temperature of the thermal conductivity detector was kept at 100° C. Helium as the carrier gas was flowed at a rate of 60 ml/min.

Figure 2:
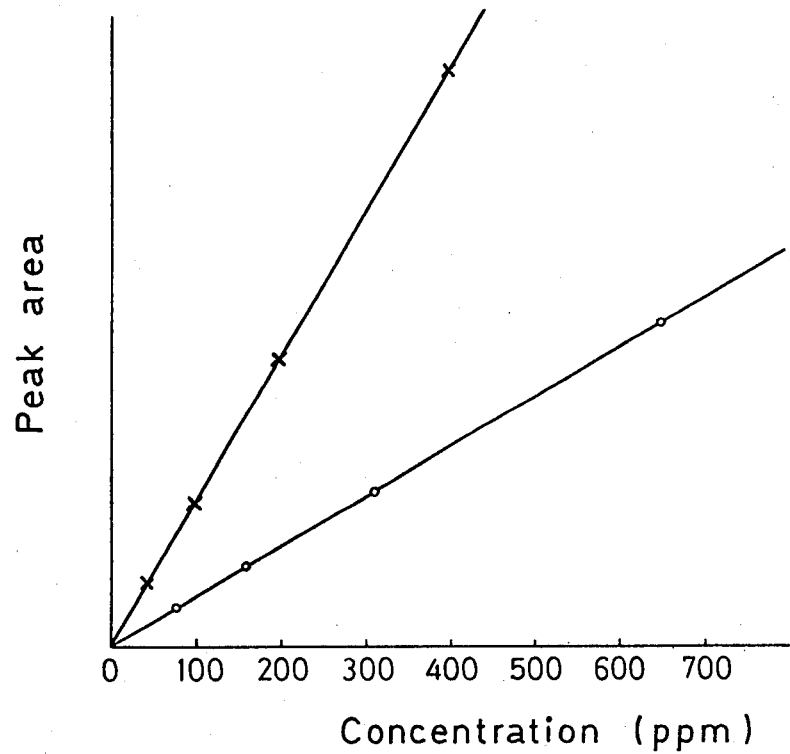
FIG. 2 is a graph of the relationship of the peak areas of $N_2$ and $CO_2$ on the chromatograph with total $N_2$ and $CO_2$ contents.

An aqueous solution containing sodium nitrate and potassium hydrogen phthalate (20 μl) was introduced into the reactor tube by the aid of a microsyringe, and calibration curves were prepared by plotting the relationships of the peak areas of nitrogen and carbon dioxide on the chromatogram with the total nitrogen and carbon contents on a graph as shown in FIG. 2 of the accompanying drawings wherein the marks (o) and (x) indicate respectively the ones of nitrogen and of carbon.

Using the calibration curves thus obtained, the total nitrogen and carbon contents in aqueous solutions of various nitrogenous and carbonaceous materials were measured.

Table 1

| Test compound | Known total content (ppm) N | Known total content (ppm) C | Measured total content (ppm) N | Measured total content (ppm) C |
|---|---|---|---|---|
| L-Methionine | 93 | 400 | 93 | 400 |
| 4-Aminoantipyrine | 127 | 400 | 128 | 401 |
| Glycine | 100 | 172 | 102 | 174 |
| Hexamethylene-tetramine | 50 | 64 | 52 | 65 |
| Polyvinyl alcohol | — | 55 | — | 57 |
| Urea | 200 | 86 | 201 | 87 |
| Sodium thiocyanate | 165 | 142 | 160 | 145 |
| Sodium hydrogen carbonate | — | 200 | — | 200 |
| Ammonium chloride | 500 | — | 502 | — |
| Pyridine + 3% NaCl | 86 | 371 | 86 | 372 |
| Glycine + 3% Na$_2$SO$_4$ | 200 | 343 | 202 | 339 |
| Aniline + 3% NaCl | 77 | 397 | 77 | 396 |

EXAMPLE 2

The total nitrogen and carbon contents in aqueous solutions of various nitrogenous and carbonaceous materials were measured in the same manner as in Example 1 but using 0.1% palladium deposited on alumina (particle size, 20 to 40 mesh; about 4 ml) in place of platinum gauze.

The results are shown in Table 2.

Table 2

| Test compound | Known total content (ppm) N | Known total content (ppm) C | Measured total content (ppm) N | Measured total content (ppm) C |
|---|---|---|---|---|
| Aniline | 39 | 198 | 39 | 196 |
| Pyridine | 86 | 371 | 84 | 372 |
| NaHCO$_3$ + 3% NaCl | — | 500 | — | 502 |
| Urea + 3% NaCl | 200 | 86 | 201 | 85 |

EXAMPLE 3

The total nitrogen contents in aqueous solutions of various nitrogenous materials were determined in the same manner as in Example 1 but using the reactor tube wherein the oxidizing agent was eliminated.

The results are shown in Table 3.

Table 3

| Test compound | Total N content (ppm) Known | Total N content (ppm) Measured |
|---|---|---|
| Sodium nitrite | 100 | 98 |
| Sodium azide | 100 | 102 |
| Sulfamic acid | 60 | 61 |
| Ammonium sulfate | 200 | 199 |

EXAMPLE 4

In a mullite pipe of 7 mm in inner diameter and 30 cm in length as the reactor tube, cylindrical platinum gauze (60 mesh; 1 cm in length) as the destructive oxidation catalyst and pelletized tricobalt tetroxide (about 6 ml; 10 to 24 mesh) as the oxidizing agent were charged separating each material from others with quartz cotton and also placing quartz cotton at the lowest part. The destructive oxidation catalyst zone was kept at 950° C, and the oxidizing agent zone was maintained at 500° C. In a stainless steel column of 1 m in length as the separation column in the gas chromatograph, silica gel (60 to 80 mesh) was charged, and the temperature of the column was set at 80° C. The temperature of the thermal conductivity detector was kept at 80° C. Helium as the carrier gas was flowed at a rate of 60 ml/min.

Using the calibration curve prepared by the use of an aqueous solution containing potassium hydrogen phthalate, the total carbon contents in aqueous solutions of various carbonaceous materials were measured. The injected amount of the specimen was 20 μl.

The results are shown in Table 4.

Table 4

| Test compound | Total C content (ppm) | |
|---|---|---|
| | Known | Measured |
| o-Cresol | 47 | 48 |
| m-Cresol | 109 | 108 |
| Glucose | 100 | 98 |
| Benzoic acid | 69 | 70 |
| Sodium β-naphthalene-sulfonate | 51 | 52 |
| m-Toluidine | 248 | 246 |
| Aniline | 623 | 638 |
| Pyridine | 742 | 745 |

EXAMPLE 5

In a quartz pipe of 7 mm in inner diameter and 20 cm in length as the reactor tube, cobalt oxide (about 3 ml) as the oxidizing agent was charged, and the temperature was kept at 800° C. In a stainless steel column of 2.5 m in length as the separation column in the gas chromatograph, silica gel (60 to 80 mesh) was charged, and the temperature of the column was maintained at 80° C. The temperature of the thermal conductivity detector was set at 80° C. Helium as the carrier gas was flowed at a rate of 40 ml/min.

Using the calibration curve prepared by the use of an aqueous solution containing potassium hydrogen phthalate, the total carbon contents in aqueous solutions of various carbonaceous materials were measured. The injected amount of the specimen was 20 μl.

The results are shown in Table 5.

Table 5

| Test compound | Total C content (ppm) | |
|---|---|---|
| | Known | Measured |
| Benzoic acid | 100 | 107 |
| Urea | 100 | 94 |
| Alanine | 100 | 96 |
| Hippuric acid | 104 | 105 |
| Glucose | 105 | 109 |
| Sodium β-naphthalene sulfonate | 98 | 97 |

EXAMPLE 6

The total carbon content in an aqueous solution of potassium hydrogen phthalate and sodium hydrogen carbonate was measured in the same manner as in Example 5 but using as th oxidizing agent(s) manganese oxide (about 3 ml) (Case A), 5% palladium deposited on asbestos (about 1 ml) and cobalt oxide (about 3 ml) (Case B) or pelletized silver (about 1 ml) and cobalt oxide (about 3 ml) (Case C).

The results are shown in Table 6.

Table 6

| Test compound | Total C content (ppm) | | | |
|---|---|---|---|---|
| | Known | Measured | | |
| | | A | B | C |
| Potassium hydrogen phthalate | 162 | 166 | 165 | 171 |
| | 810 | 799 | 816 | 832 |
| Sodium hydrogen carbonate | 100 | 109 | 97 | 104 |
| | 500* | — | — | — |

Note: *Standard for measurement

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An analytical method for determination of the total nitrogen and/or carbon contents in an aqueous solution containing nitrogenous and/or carbonaceous materials as a specimen, which comprises introducing the aqueous solution with an inert gas containing substantially no nitrogen and/or carbon dioxide as a carrier gas into a reactor tube packed with a destructive oxidation catalyst and/or a reducing agent and/or an oxidizing agent, maintaining the reaction tube at elevated temperatures so as to decompose the nitrogenous and/or carbonaceous materials to nitrogen and/or carbon dioxide and measuring the amounts of nitrogen and/or carbon dioxide in the resulting gaseous mixture from the reactor tube by the use of a thermal conductivity gas chromatograph.

2. The method according to claim 1, wherein the reactor tube is packed with a destructive oxidation catalyst, a reducing agent and an oxidizing agent.

3. The method according to claim 2, wherein the destructive oxidation catalyst, the reducing agent and the oxidizing agent are heated at 700° to 1200° C, at 300° to 700° C and at 300° to 700° C, respectively.

4. The method according to claim 1, wherein the reactor tube is packed with a destructive oxidation catalyst and a reducing agent.

5. The method according to claim 4, wherein the destructive oxidation catalyst and the reducing agent are heated at 700° to 1200° C and at 300° to 700° C, respectively.

6. The method according to claim 1, wherein the reactor tube is packed with a destructive oxidation catalyst and an oxidizing agent.

7. The method according to claim 6, wherein the destructive oxidation catalyst and the oxidizing agent are heated at 700° to 1200° C and at 300° to 700° C, respectively.

8. The method according to claim 6, wherein the destructive oxidation catalyst and the oxidizing agent are heated at 700° to 1200° C.

9. The method according to claim 1, wherein the reactor tube is packed with an oxidizing agent.

10. The method according to claim 9, wherein the oxidizing agent is heated at 700° to 1200° C.

11. The method according to claim 1, wherein the destructive oxidation catalyst comprises at least one metal selected from the group consisting of metals belonging to Group IB or VIII in the periodic table.

12. The method according to claim 11, wherein the metal is platinum or palladium.

13. The method according to claim 1, wherein the reducing agent comprises at least one metal selected from the group consisting of copper, nickel, iron, cobalt and zinc.

14. The method according to claim 13, wherein the metal is reduced copper or reduced nickel.

15. The method according to claim 1, wherein the oxidizing agent comprises at least one oxide selected from the group consisting of oxides of cobalt, nickel, vanadium, tungsten, silver and manganese.

16. The method according to claim 15, wherein the oxide is oxides of cobalt.

17. An analytical method for determination of the total nitrogen and carbon contents in an aqueous solution containing nitrogenous and carbonaceous materials as a specimen, which comprises introducing the aqueous solution with an inert gas containing substantially no nitrogen and carbon dioxide as a carrier gas into a reactor tube packed with a destructive oxidation catalyst, a reducing agent and an oxidizing agent so as to decompose the nitrogenous and carbonaceous materials respectively to nitrogen and carbon dioxide and measuring the amounts of nitrogen and carbon dioxide in the resulting gaseous mixture from the reactor tube by the use of a thermal conductivity gas chromatograph, the destructive oxidation catalyst, the reducing agent and the oxidizing agent being heated at 700° to 1200° C, at 300° to 700° C and at 300° to 700° C, respectively.

18. The method according to claim 17, wherein the inert gas is helium.

19. The method according to claim 17, wherein the reactor tube is packed with the destructive oxidation catalyst, the reducing agent and the oxidizing agent in this order.

20. An analytical method for determination of the total nitrogen content in an aqueous solution containing nitrogenous materials as a specimen, which comprises introducing the aqueous solution with an inert gas containing substantially no nitrogen as a carrier gas into a reactor tube packed with a destructive oxidation catalyst and a reducing agent so as to decompose the nitrogenous materials to nitrogen and measuring the amount of nitrogen in the resulting gaseous mixture from the reactor tube by the use of a thermal conductivity gas chromatograph, the destructive oxidation catalyst and the reducing agent being heated at 700° to 1200° C and at 300° to 700° C, respectively.

21. An analytical method for determination of the total carbon content in an aqueous solution containing carbonaceous materials as a specimen, which comprises introducing the aqueous solution with an inert gas containing substantially no carbon dioxide as a carrier gas into a reactor tube packed with a destructive oxidation catalyst and an oxidizing agent so as to decompose the carbonaceous materials to carbon dioxide and measuring the amount of carbon dioxide in the resulting gaseous mixture from the reactor tube by the use of a thermal conductivity gas chromatograph, the destructive oxidation catalyst and the oxidizing agent being heated at 700° to 1200° C and at 300° to 700° C, respectively.

22. An analytical method for determination of the total carbon content in an aqueous solution containing carbonaceous materials as a specimen, which comprises introducing the aqueous solution with an inert gas containing substantially no carbon dioxide as a carrier gas into a reactor tube packed with a destructive oxidation catalyst and an oxidizing agent so as to decompose the carbonaceous materials to carbon dioxide and measuring the amount of carbon dioxide in the resulting gaseous mixture from the reactor tube by the use of a thermal conductivity gas chromatograph, the destructive oxidation catalyst and the oxidizing agent being heated at 700° to 1200° C.

23. An analytical method for determination of the total carbon content in an aqueous solution containing carbonaceous materials as a specimen, which comprises introducing the aqueous solution with an inert gas containing substantially no carbon dioxide as a carrier gas into a reactor tube packed with an oxidizing agent so as to decompose the carbonaceous materials to carbon dioxide and measuring the amount of carbon dioxide in the resulting gaseous mixture from the reactor tube by the use of a thermal conductivity gas chromatograph, the oxidizing agent being heated at 700° to 1200° C.

24. An analytical apparatus for determination of the total nitrogen and/or carbon contents in an aqueous solution containing nitrogenous and/or carbonaceous materials as a specimen, which comprises a reactor tube provided with an inlet and an outlet, said reactor tube being packed with a destructive oxidation catalyst and/or a reducing agent and/or an oxidizing agent, supply means for introducing an inert gas containing substantially no nitrogen and/or carbon dioxide into the inlet of the reactor tube, an injection means for introducing the specimen to be analyzed into the inlet of the reactor tube, moisture removal means for removing moisture from the gaseous mixture produced in the reaction tube, said moisture removal means being disposed downstream from the outlet of the reactor tube, a gas chromatograph provided with a thermal conductivity detector, and disposed downstream of said moisture removal means, and conduit means for providing connection between the reactor tube, the moisture removal means and said gas chromatograph.

25. The method of claim 1, wherein the inert carrier gas is an oxygen-free gas.

* * * * *